US008844112B2

(12) United States Patent
Snow et al.

(10) Patent No.: US 8,844,112 B2
(45) Date of Patent: Sep. 30, 2014

(54) METHODS OF MANUFACTURING SAFETY SHIELDS FOR MEDICAL NEEDLES AND RELATED MANUFACTURING DEVICES

(75) Inventors: Jeremy W. Snow, North Salt Lake, UT (US); F. Mark Ferguson, Salt Lake City, UT (US); Roy L. Barrus, Centerville, UT (US)

(73) Assignee: Specialized Health Products, Inc., Salt Lake City, UT (US)

( * ) Notice: Subject to any disclaimer, the term of this patent is extended or adjusted under 35 U.S.C. 154(b) by 2079 days.

(21) Appl. No.: 11/918,520

(22) PCT Filed: Apr. 18, 2006

(86) PCT No.: PCT/US2006/014497
§ 371 (c)(1),
(2), (4) Date: Oct. 12, 2007

(87) PCT Pub. No.: WO2006/113675
PCT Pub. Date: Oct. 26, 2006

(65) Prior Publication Data
US 2009/0038135 A1    Feb. 12, 2009

Related U.S. Application Data

(60) Provisional application No. 60/672,283, filed on Apr. 18, 2005.

(51) Int. Cl.
*B23Q 3/00* (2006.01)
*A61M 5/32* (2006.01)
*B23P 11/00* (2006.01)
*B21D 35/00* (2006.01)

(52) U.S. Cl.
CPC ......... *A61M 5/3273* (2013.01); *A61M 2207/10* (2013.01)
USPC ................ 29/464; 29/469.5; 29/434; 29/428; 604/164.08; 604/192

(58) Field of Classification Search
USPC .......... 29/434, 432.1, 432.2, 445, 469.5, 428, 29/464; 604/48, 93.01, 164.01, 164.08, 604/181, 187, 192, 263
See application file for complete search history.

(56) References Cited

U.S. PATENT DOCUMENTS 4,929,241 A * 5/1990 Kulli .............................. 604/263
5,152,751 A * 10/1992 Kozlowski .................... 604/192

(Continued)

FOREIGN PATENT DOCUMENTS

EP          1306052 A1 *  5/2003  ............. A61B 5/145
WO     WO 90/08564 A1 *  8/1990  ............. A61M 5/32

(Continued)

OTHER PUBLICATIONS

PCT/US2006/014497 filed Apr. 18, 2006 International Search Report dated Nov. 14, 2008.

(Continued)

*Primary Examiner* — Essama Omgba
(74) *Attorney, Agent, or Firm* — Rutan & Tucker LLP

(57) ABSTRACT

A medical needle shield apparatus is manufactured by positioning a portion of a friction plate or clip on a medical needle and then further orienting the remaining portion so that the tolerance is optimized for resetting the clip on the medical needle.

7 Claims, 15 Drawing Sheets

(56) References Cited

U.S. PATENT DOCUMENTS

| | | | | |
|---|---|---|---|---|
| 5,205,829 A * | 4/1993 | Lituchy | | 604/164.08 |
| 5,401,252 A * | 3/1995 | Deal | | 604/192 |
| 5,445,619 A * | 8/1995 | Burns | | 604/192 |
| 5,498,242 A * | 3/1996 | Cooke | | 604/192 |
| 5,599,310 A * | 2/1997 | Bogert | | 604/164.12 |
| 5,599,313 A * | 2/1997 | Gyure et al. | | 604/192 |
| 5,738,660 A * | 4/1998 | Luther | | 604/164.08 |
| 5,746,726 A * | 5/1998 | Sweeney et al. | | 604/263 |
| 5,868,716 A * | 2/1999 | Sweeney et al. | | 604/263 |
| 6,004,294 A * | 12/1999 | Brimhall et al. | | 604/164.08 |
| 6,298,541 B1 | 10/2001 | Newby et al. | | 29/458 |
| 6,436,086 B1 * | 8/2002 | Newby et al. | | 604/507 |
| 6,440,104 B1 * | 8/2002 | Newby et al. | | 604/192 |
| 6,592,556 B1 * | 7/2003 | Thorne | | 604/192 |
| 6,595,955 B2 | 7/2003 | Ferguson et al. | | |
| 6,648,855 B2 * | 11/2003 | Crawford et al. | | 604/110 |
| 6,682,510 B2 * | 1/2004 | Niermann | | 604/263 |
| 6,699,217 B2 * | 3/2004 | Bennett et al. | | 604/110 |
| 6,780,169 B2 * | 8/2004 | Crawford | | 604/110 |
| 6,796,962 B2 * | 9/2004 | Ferguson et al. | | 604/110 |
| 6,902,546 B2 * | 6/2005 | Ferguson | | 604/110 |
| 6,972,002 B2 * | 12/2005 | Thorne | | 604/164.08 |
| 7,004,927 B2 | 2/2006 | Ferguson et al. | | |
| 7,128,726 B2 * | 10/2006 | Crawford et al. | | 604/110 |
| 7,179,244 B2 | 2/2007 | Smith et al. | | |
| 7,220,249 B2 * | 5/2007 | Hwang et al. | | 604/263 |
| 7,223,258 B2 * | 5/2007 | Crawford | | 604/192 |
| 7,357,784 B2 * | 4/2008 | Ferguson | | 604/110 |
| 7,413,562 B2 | 8/2008 | Ferguson et al. | | |
| 7,428,773 B2 * | 9/2008 | Newby et al. | | 29/458 |
| 7,537,581 B2 * | 5/2009 | Hwang | | 604/110 |
| 7,611,485 B2 * | 11/2009 | Ferguson | | 604/110 |
| 7,618,395 B2 * | 11/2009 | Ferguson | | 604/110 |
| 8,231,583 B2 * | 7/2012 | Swenson | | 604/198 |
| 8,277,408 B2 * | 10/2012 | Crawford et al. | | 604/110 |
| 8,403,886 B2 * | 3/2013 | Bialecki et al. | | 604/110 |
| 2002/0151852 A1 * | 10/2002 | Crawford et al. | | 604/197 |
| 2002/0151853 A1 * | 10/2002 | Crawford | | 604/197 |
| 2002/0156425 A1 * | 10/2002 | Crawford et al. | | 604/192 |
| 2002/0161336 A1 * | 10/2002 | Crawford et al. | | 604/192 |
| 2002/0193745 A1 * | 12/2002 | Ferguson | | 604/192 |
| 2003/0100868 A1 * | 5/2003 | Ferguson et al. | | 604/263 |
| 2003/0135157 A1 * | 7/2003 | Saulenas et al. | | 604/110 |
| 2003/0181868 A1 * | 9/2003 | Swenson | | 604/263 |
| 2003/0187398 A1 * | 10/2003 | Crawford | | 604/192 |
| 2003/0187399 A1 * | 10/2003 | Crawford | | 604/192 |
| 2003/0220614 A1 * | 11/2003 | Crawford | | 604/192 |
| 2003/0220618 A1 * | 11/2003 | Crawford | | 604/263 |
| 2004/0059302 A1 * | 3/2004 | Crawford et al. | | 604/263 |
| 2004/0078003 A1 | 4/2004 | Smith et al. | | |
| 2004/0092888 A1 * | 5/2004 | Ferguson et al. | | 604/263 |
| 2004/0138613 A1 * | 7/2004 | Reid | | 604/93.01 |
| 2004/0186439 A1 * | 9/2004 | Crawford et al. | | 604/197 |
| 2004/0215154 A1 * | 10/2004 | Hwang et al. | | 604/263 |
| 2004/0236289 A1 * | 11/2004 | Ferguson et al. | | 604/263 |
| 2005/0004531 A1 * | 1/2005 | Hwang et al. | | 604/263 |
| 2005/0043691 A1 * | 2/2005 | Ferguson | | 604/263 |
| 2005/0059937 A1 * | 3/2005 | Ferguson | | 604/263 |
| 2005/0070855 A1 * | 3/2005 | Ferguson et al. | | 604/263 |
| 2005/0124944 A1 * | 6/2005 | Hwang | | 604/263 |
| 2005/0148942 A1 * | 7/2005 | Newby et al. | | 604/192 |
| 2005/0245879 A9 * | 11/2005 | Crawford | | 604/192 |
| 2006/0015073 A9 * | 1/2006 | Ferguson et al. | | 604/198 |
| 2006/0074387 A1 * | 4/2006 | Thorne et al. | | 604/263 |
| 2006/0129106 A1 * | 6/2006 | Ferguson et al. | | 604/198 |
| 2006/0270947 A1 * | 11/2006 | Crawford et al. | | 600/576 |
| 2007/0106224 A1 * | 5/2007 | Hwang | | 604/192 |
| 2008/0033362 A1 * | 2/2008 | Hwang et al. | | 604/164.08 |
| 2008/0208138 A1 * | 8/2008 | Lim et al. | | 604/192 |
| 2009/0024092 A1 * | 1/2009 | Newby et al. | | 604/192 |
| 2009/0038135 A1 * | 2/2009 | Snow et al. | | 29/428 |
| 2009/0054852 A1 * | 2/2009 | Takano et al. | | 604/263 |
| 2009/0131876 A1 * | 5/2009 | Coyne | | 604/198 |
| 2009/0157013 A1 * | 6/2009 | Wong | | 604/263 |
| 2009/0216201 A1 * | 8/2009 | Meehan et al. | | 604/263 |
| 2010/0191188 A1 * | 7/2010 | Harding et al. | | 604/164.08 |
| 2010/0191189 A1 * | 7/2010 | Harding et al. | | 604/164.08 |
| 2012/0296289 A1 * | 11/2012 | Albert et al. | | 604/263 |

FOREIGN PATENT DOCUMENTS

| | | | | |
|---|---|---|---|---|
| WO | WO 93/18809 A1 * | 9/1993 | | A61M 5/32 |
| WO | WO 02098481 A2 * | 12/2002 | | |
| WO | 2004014464 A1 | 2/2004 | | |
| WO | 2004043521 A1 | 5/2004 | | |
| WO | 2004060138 A2 | 7/2004 | | |
| WO | 2004091687 A2 | 10/2004 | | |
| WO | 2005053774 A1 | 6/2005 | | |
| WO | 2005060679 A2 | 7/2005 | | |

OTHER PUBLICATIONS

PCT/US2006/014497 filed Apr. 18, 2006 Written Opinion dated Nov. 14, 2008.

* cited by examiner

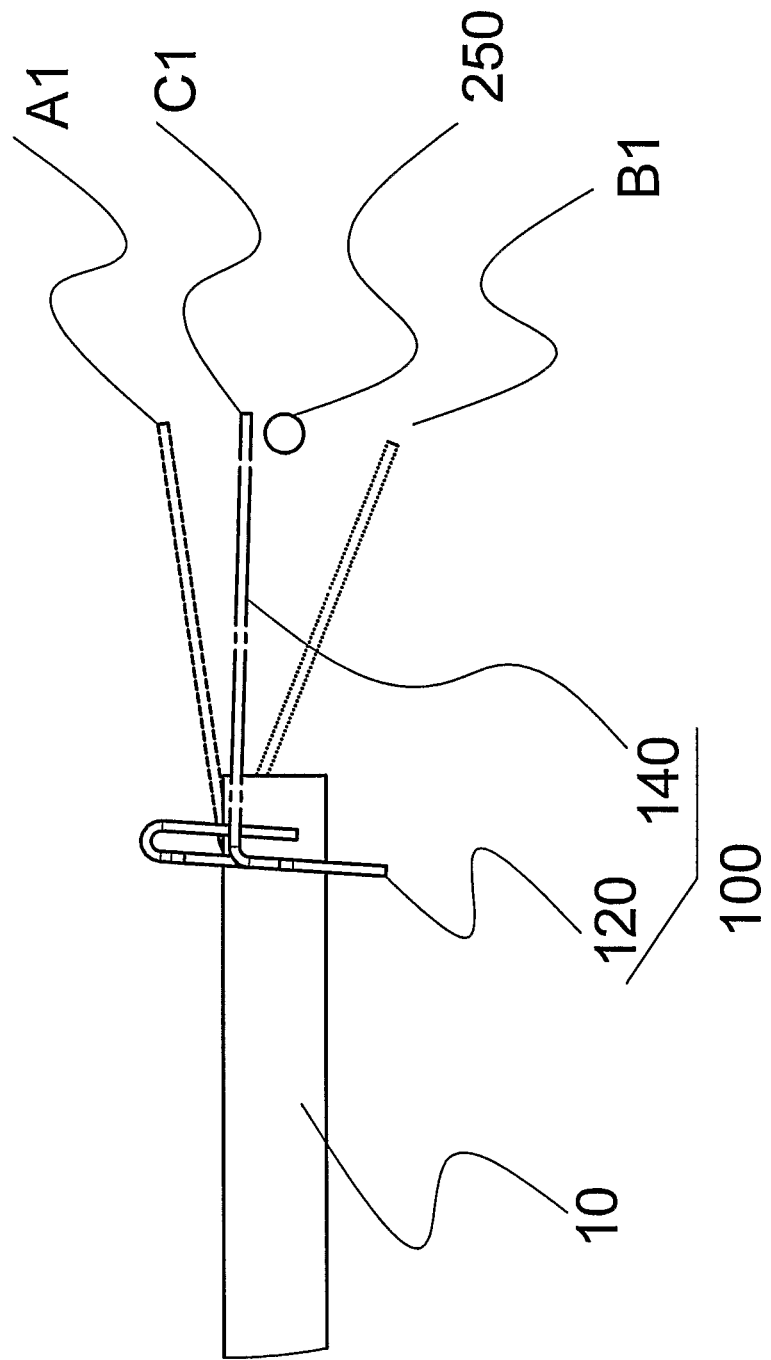

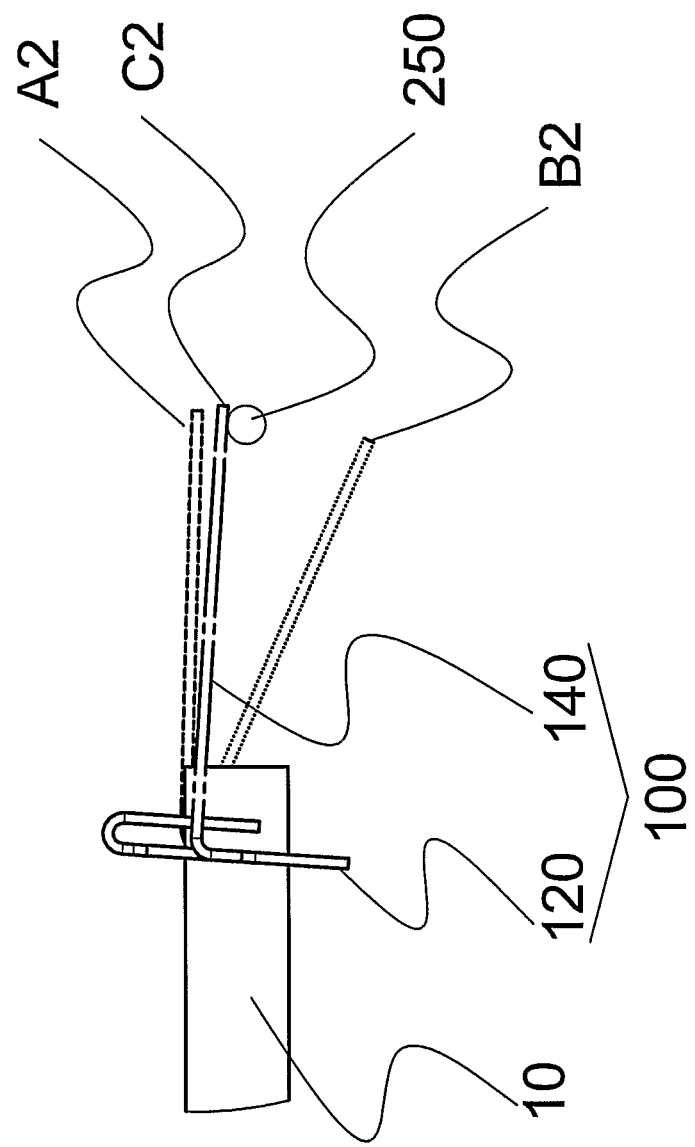

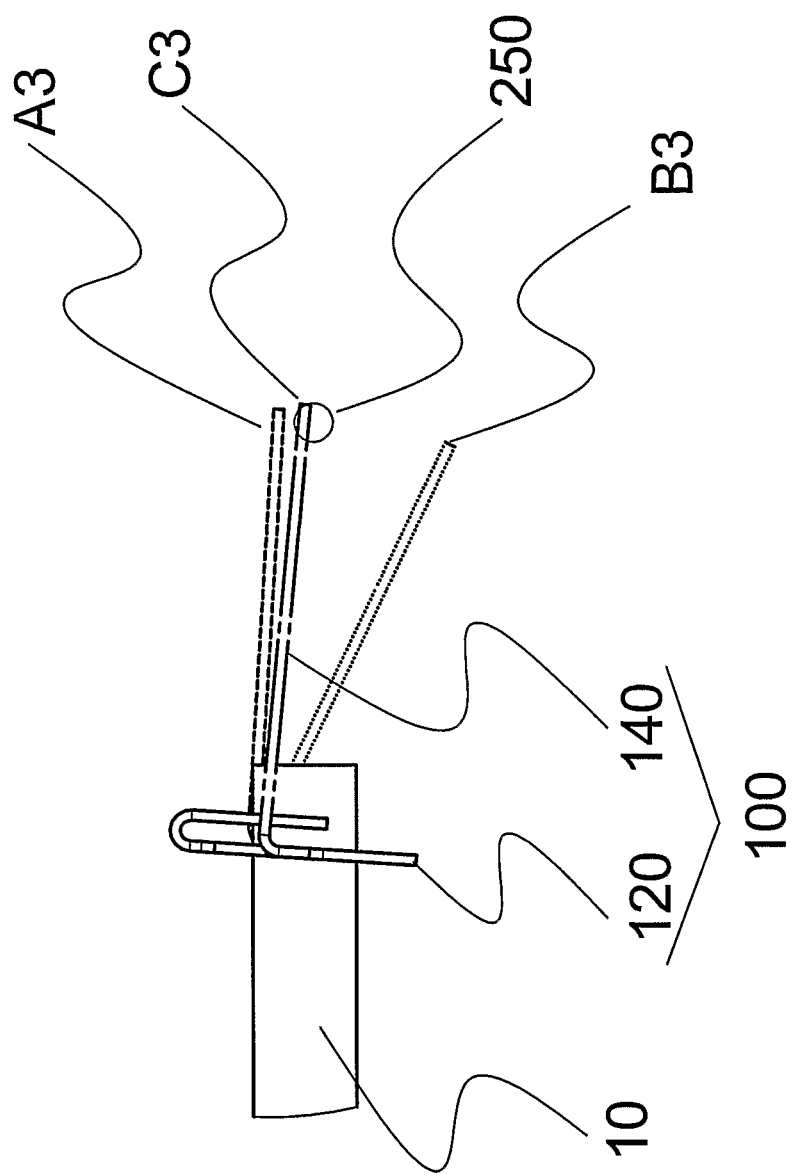

METHODS OF MANUFACTURING SAFETY SHIELDS FOR MEDICAL NEEDLES AND RELATED MANUFACTURING DEVICES

PRIORITY

This application is a U.S. national stage application under 35 U.S.C. §371 of International Application No. PCT/US2006/014497, filed Apr. 18, 2006, claiming priority to U.S. Provisional Application No. 60/672,283, filed Apr. 18, 2005, each of which is incorporated by reference in its entirety into this application.

TECHNICAL FIELD

The present invention relates generally to safety shields for medical needles, and more particularly, to safety shields that protect a needle point of a medical needle.

DESCRIPTION OF THE RELATED ART

The present disclosure generally relates to safety shields for medical needles, and more particularly, to safety shields that protect a needle point of a medical needle.

Problems associated with inadvertent needle sticks are well known in the art of blood sampling, percutaneous medication injection and other medical procedures involving use of medical needles. Significant attention has been focused on needle stick problems due to the contemporary sensitivity of exposure to AIDS, Hepatitis and other serious blood-borne pathogen exposures.

Procedures for removing a needle from a patient commonly require a technician to use one hand to place pressure at the wound site where the needle is being withdrawn, while removing the needle device with the other hand. It is also common practice for an attending technician to give higher priority to care for the patient than is given to disposal of a needle. In the case of typical needle devices without safety shields, such priority either requires the convenience of an available sharps container within reach or another means for safe disposal without leaving the patient's side. Providing adequate care while following safety procedures is often compounded by the patient's physical condition and mental state, such as in burn units and psychiatric wards. Under such conditions, it is difficult to properly dispose of a used needle while caring for a patient.

The widespread knowledge and history associated with needle care and disposal problems have resulted in numerous devices for preventing accidental needle sticks. Problems of current safety devices include difficulty of use and high cost due to their complexity and number of parts.

Other known devices employ sheaths that are spring activated, telescoping, pivoting, etc. These devices, however, may disadvantageously misfire or be cumbersome to activate. Further drawbacks of current devices include high manufacturing cost due to complexity and the number of parts. Thus, these type prior art devices may not adequately and reliably shield medical needle apparatus to prevent hazardous exposure.

Consequently, there remains a need to provide a more satisfactory solution for needle safety devices by overcoming the disadvantages and drawbacks of the prior art. Therefore, it would be desirable to provide a more adequate and reliable medical needle shield apparatus that employs a safety shield slidably movable along a medical needle to prevent hazardous exposure to a needle tip. It would be advantageous to provide such a safety shield that is capable of being reset to safely allow re-use of certain needle apparatus. Such a needle shield apparatus should be easily and reliably movable to shield a needle tip of a needle cannula.

BRIEF DESCRIPTION OF THE DRAWINGS

Understanding that drawings depict only typical embodiments of the invention and are not therefore to be considered to be limiting of its scope, the invention will be described and explained with additional specificity and detail through the use of the accompanying drawings as listed below.

FIG. 1 also depicts a shaping device having a needle anchor to hold the medical needle and binding member retention tools.

FIG. 2 also shows the end sensing member orientation tools with a top component engaging the end sensing members

FIGS. 5-7 depict another embodiment.

FIG. 6 shows a view like FIG. 3 except that the sensor (not shown in FIG. 6) is being utilized in this embodiment.

FIG. 7 shows a view like FIG. 4 except that the position of the sensor is shown as utilized in this embodiment.

FIGS. 8-12 depict another embodiment.

FIG. 9 shows a view like FIG. 3.

FIG. 10 shows a view like FIG. 4.

FIG. 11 shows incremental revisions to the orientation of the end sensing members to "nudge" the end sensing members into a final orientation. FIG. 11 shows the top component of the end sensing member orientation tools displacing the end sensing members and shows a prior displacement in phantom lines.

FIG. 12 shows a view like FIG. 4 and FIG. 7 except that the position of the end sensing members in FIG. 12 is not the same as those in FIG. 4 and FIG. 7.

FIG. 13 is a schematic view of the three states including the initial or previous orientation, the deflected position, and the relaxed orientation.

FIG. 14 is a schematic view of the three states achieved after the movement of the end sensing members shown in FIG. 13.

FIG. 15 is a schematic view of the three states achieved after the movement of the end sensing members shown in FIG. 14.

DETAILED DESCRIPTION OF THE EXEMPLARY EMBODIMENTS

The exemplary embodiments of the medical needle shield apparatus and methods of manufacture disclosed are discussed in terms of medical needles for infusion of intravenous fluids, medication infusion or fluid collection, guiding of other needles, e.g., biopsy, and more particularly, in terms of needle shield apparatus employed with a needle cannula that prevent hazardous exposure to the needle tip, including, for example, inadvertent needle sticks. It is envisioned that the present disclosure, however, finds application to a wide variety of cannula needles and devices for the infusion of preventive medications, medicaments, therapeutics, etc. to a subject, such as, for example, epidural needles, spinal needles, biopsy needles, chiba needles, potts cournand needles, coaxial introducer needles, Y-sites, etc. It is also envisioned that the present disclosure may be employed for collection of body fluids and/or tissues, including those employed during procedures relating to soft tissue biopsy, bone biopsy, phlebotomy, digestive, intestinal, urinary, veterinary, etc. It is contemplated that the medical needle shield apparatus may be utilized with other medical needle applications including, but not limited to, fluid infusion, fluid collection, catheters, catheter introducers, guidewire introducers, biopsy needle introducers, spinal and epidural, biopsy, aphaeresis, dialysis, blood donor, Veress needles, Huber needles, etc.

In the discussion that follows, the term "proximal" refers to a portion of a structure that is closer to a clinician, and the term "distal" refers to a portion that is further from the clinician. As used herein, the term "subject" refers to a patient that receives infusions or has blood and/or fluid collected therefrom using the medical needle shield apparatus. According to the present disclosure, the term "clinician" refers to an individual administering an infusion, performing fluid or tissue collection, installing or removing a needle cannula from a medical needle shield apparatus and may include support personnel.

The following discussion includes a description of some of the components of a medical needle shield apparatus, followed by a description of the method of manufacturing the medical needle shield apparatus in accordance with the present disclosure. Reference will now be made in detail to the exemplary embodiments of the disclosure, which are illustrated in the accompanying figures.

Figure 5:
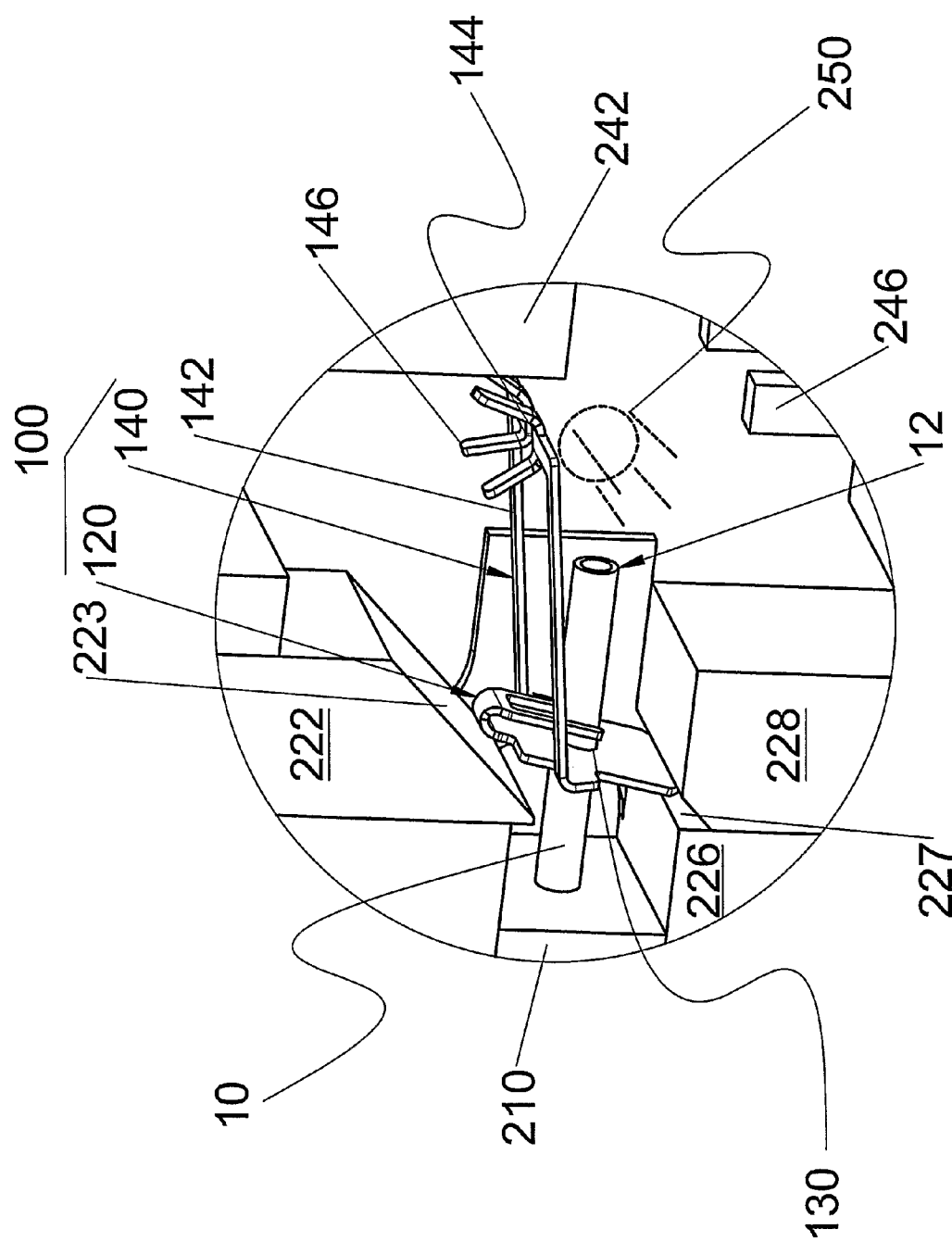
FIG. 5 is a perspective view like FIG. 1 except that a sensor is shown being utilized.
Figure 6:
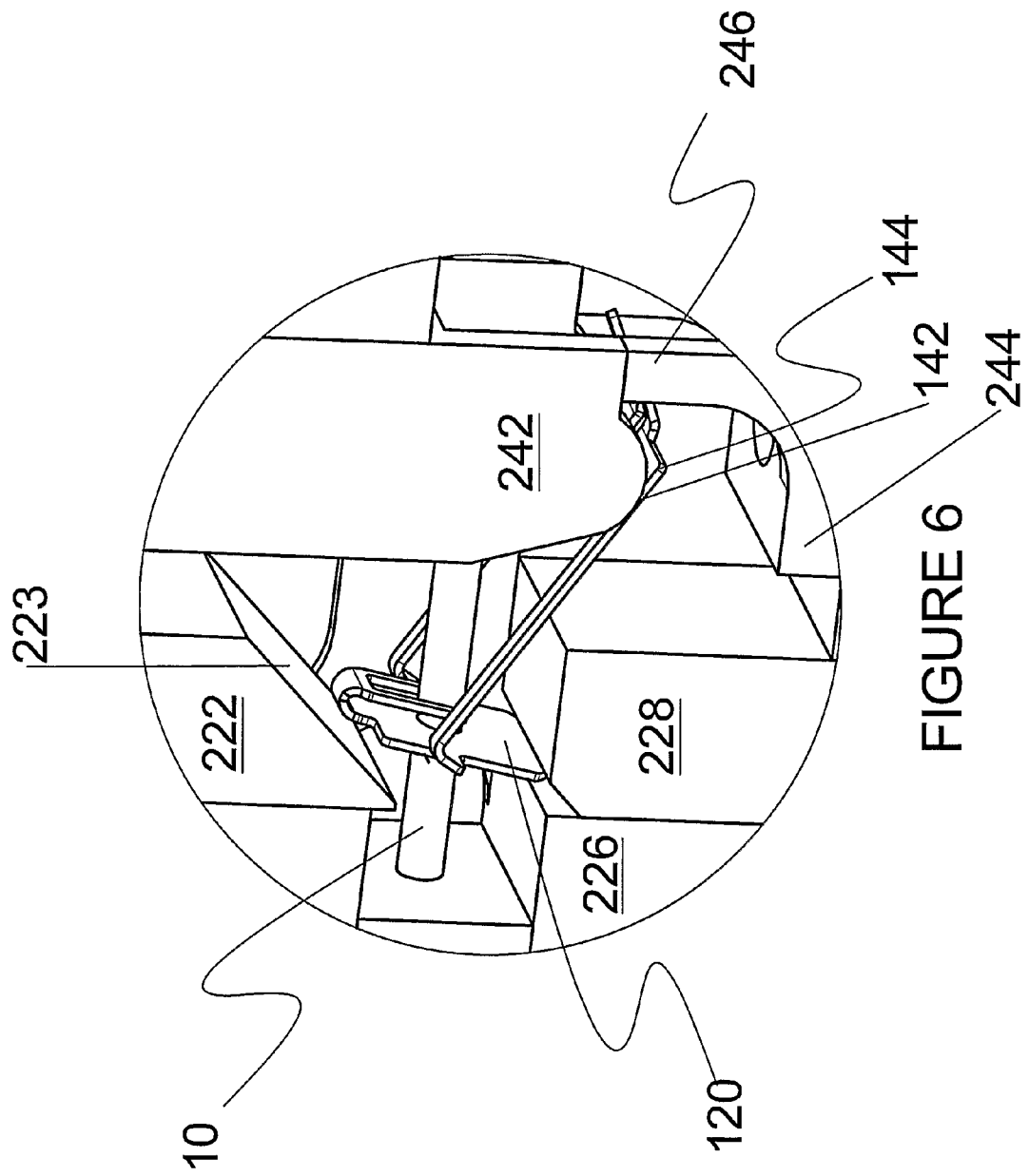
Figure 7:
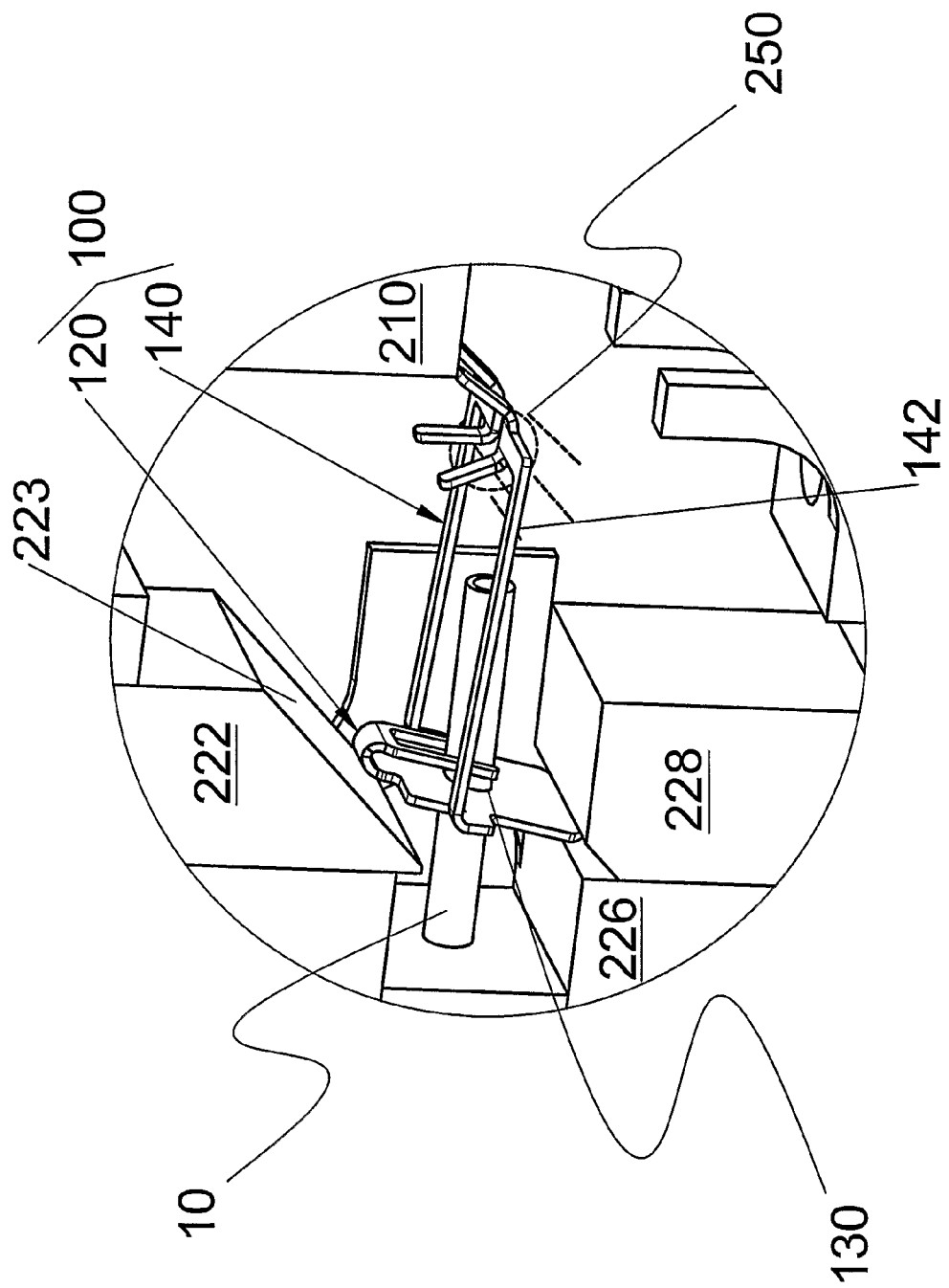

In the figures, like components are designated by like reference numerals throughout the several views. FIGS. 1-15 depict a medical needle 10 and a clip or a binding member such as a friction based single aperture plate as shown at 100. FIGS. 1-15 depict a clip 100 which has been at least partially formed and partially positioned on needle 10 to be further shaped as part of a method of manufacturing a medical needle shield apparatus. FIGS. 1-4 depict one embodiment of a method of manufacturing a medical needle shield apparatus and device used in the manufacturing process. FIGS. 5-7 depict another embodiment. FIGS. 8-12 depict yet another embodiment for constructing a medical needle shield in accordance with the principles of the present disclosure.

The components of examples of medical needle shield apparatus, such as friction based plates and other clips or binding members, are disclosed in U.S. patent application Ser. No. 10/721,526 titled Resettable Safety Shield for Medical Needles which was filed on Nov. 25, 2003 and was published as U.S. Patent Publication No. 2004/0078003. Numerous examples of friction based plates and various embodiments of medical needle shield apparatus are also disclosed in International Patent Application No. PCT/US2004/039400 which was filed on Nov. 23, 2004 and was published as International Publication No. WO 2005/053774 on Jun. 16, 2005, PCT/US2003/022093 which was filed on Jul. 14, 2003 and was published as International Publication No. WO 2004/014464, PCT/US2003/032577 which was filed on Oct. 15, 2003 and was published as International Publication No. WO 2004/043521, PCT/US2003/038340 which was filed on Dec. 2, 2003 and was published as International Publication No. WO 2004/060138, PCT/US2004/010800 which was filed on Apr. 5, 2004 and was published as International Publication No. WO 2004/091687, PCT/US2004/042560 which was filed on Dec. 17, 2004 and was published as International Publication No. WO 2005/060679. U.S. Patent Publication No. 2004/0078003 and International Publication Nos. WO 2005/053774, WO 2004/014464, WO 2004/043521, WO 2004/060138, WO 2004/091687, and WO 2005/060679 are hereby incorporated by reference.

Each friction based single aperture plate 100 has a binding member 120 and at least one end sensing member. In the embodiments depicted, each plate has dual end sensing members as identified at 140. The dual end sensing members comprise arms 142, extensions 144 and friction elements 146. After plate 100 is positioned on a needle and the medical needle shield apparatus is fully assembled, the apparatus can be used. After medical needle 10 is used in a procedure, plate 100 is pushed towards the tip 12 of needle 10 until friction elements 146 extend past tip 12. When friction elements 146 move past tip 12, plate 100 cants. Canting of plate 100 causes the perimeter which defines aperture 130 of binding member 120 to bind against needle 10. More particularly, binding member 120 includes a substantially planar aperture plate with binding surfaces that form aperture 130. Plate 100 can be reset on needle 10 to enable needle 10 to be used again by repositioning friction elements 146 to frictionally engage needle 10. Plate 100 is generally located within a housing (not shown) when used.

In certain applications, it may be desirable to control aspects of the friction based single aperture plate or a similar clip. In a resetting application it is desirable for the end sensing members to reside in a certain location or range of locations after activation. The location of the end sensing member has effects on resetting performance characteristics (e.g. repeatability, reliability, etc.). The location of the end sensing members depend on several variables (e.g. plate thickness, aperture hole size, needle diameter, and end sensing forming angle) and their respective tolerances. The full ranges of these variables and tolerances, yield end sensing member locations and ranges of locations that are outside the desired limits to achieve optimal ease in resetting plate 100.

The properties of the metal friction based aperture plate can be used to control the placement of the end sensing members. First, a plate is obtained which has components that have set perimeters and which have been shaped to have an initial orientation. Second, the binding member of the plate is positioned on the medical needle in an actuated state. Third, the end sensing members are further shaped to have a final orientation while the binding member of the plate is positioned on the medical needle. More specifically, the arms, friction elements and other components of the end sensing members are further shaped. Further shaping the end sensing members while the binding member is on the medical needle enables the end sensing members to be more accurately placed in a desired location. By placing the binding member on the needle in an actuated state, all of the variables (e.g. plate thickness, aperture hole size, and end sensing forming angle) are accounted for and the end sensing members can be further shaped and adjusted to optimize the ability of the plate to be reset. Also, in processing each binding member on each individual needle there are no tolerances that need to be accounted for. By intentionally leaving the end sensing members not fully shaped, the method allows for accurate end sensing member location and improves resetting performance characteristics. In addition to the arms and friction elements, it is also envisioned that these same principles can be applied to other components or features of the friction based single aperture plate, such as the extensions 144 which support the friction elements and extend from the arms in order to place the friction element in a desired location, etc.

In one embodiment, shown in FIGS. 1-4, the binding member 120 is in an activated state on needle 10. End sensing members 140 are in an initial orientation and are then further shaped to have a final orientation.

Figure 1:
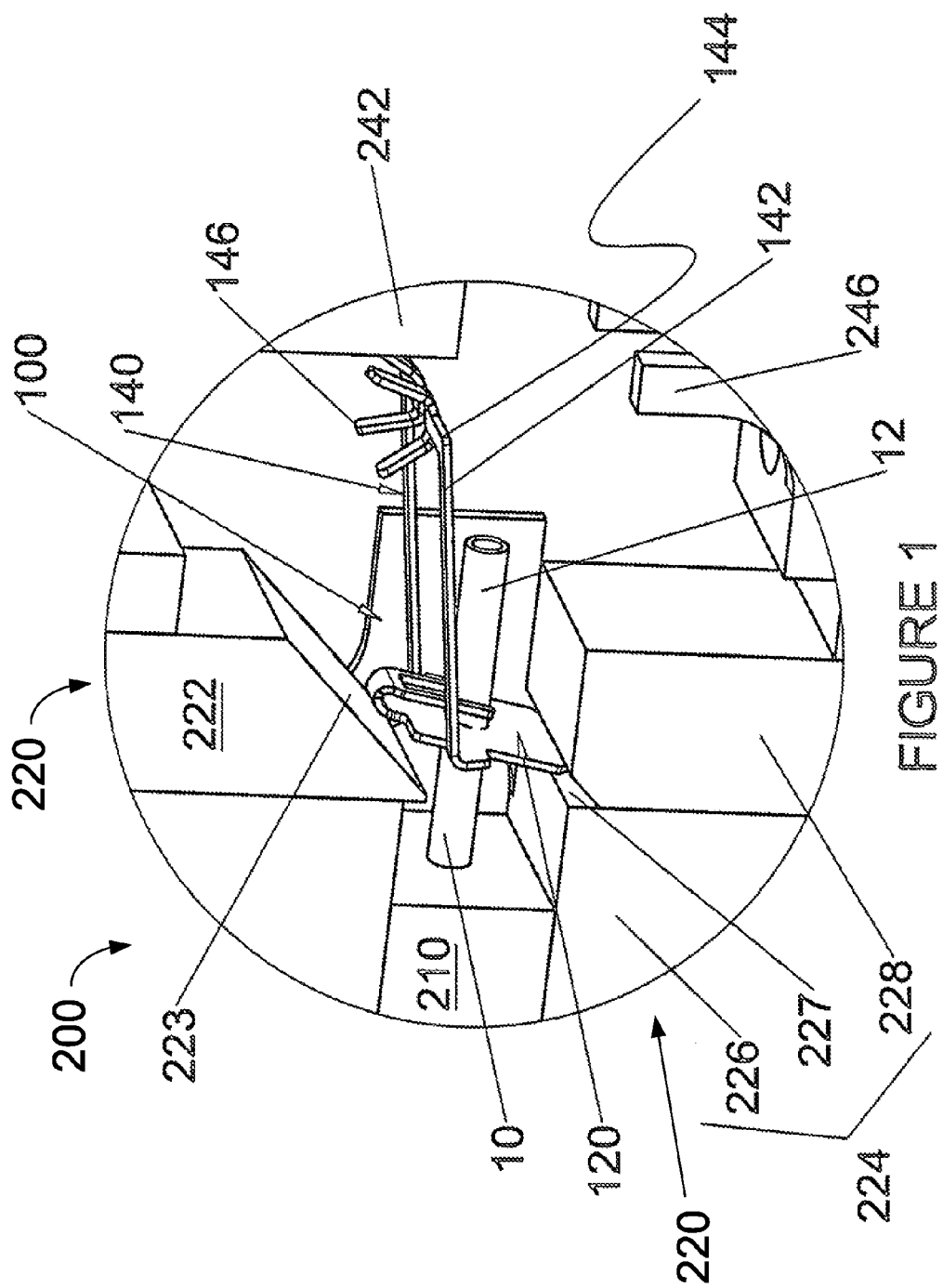
FIG. 1 is a perspective view of a friction based plate or clip with a portion on a medical needle. The remaining portion is off the medical needle and is ready to be re-oriented so that the tolerance is optimized for resetting the clip on the medical needle. The portion on the medical needle is a binding member and the portion off the needle comprises dual end sensing members.

In FIG. 1, a shaping device 200 is shown having a needle anchor 210 which holds medical needle 10. Shaping device 200 also has a plurality of components which act on binding member 120 and are collectively referred to as the binding member retention tools 220. Tools 220 comprise a top component 222 and a bottom component 224. Bottom component 224 is shown with a rear portion 226 separated by a groove 227 from a front portion 228. In one embodiment, plate 100 is pushed onto needle 10 until the back of binding member 120 abuts rear portion 226 and then front portion 228 is advanced toward rear portion 226 such that the base of binding member 120 sits in groove 227. Top component 222 is then directed against the top of binding member 120. Note that while a single retention tool can also be used to hold binding member 120 this embodiment has several advantageous abilities. For example, top component 222 has an inclined surface 223 facing the top of binding member 120, which enables it to cause the base of binding member to pivot in groove 227 to give plate 100, particularly end sensing member 140, a desired orientation.

Figure 2:
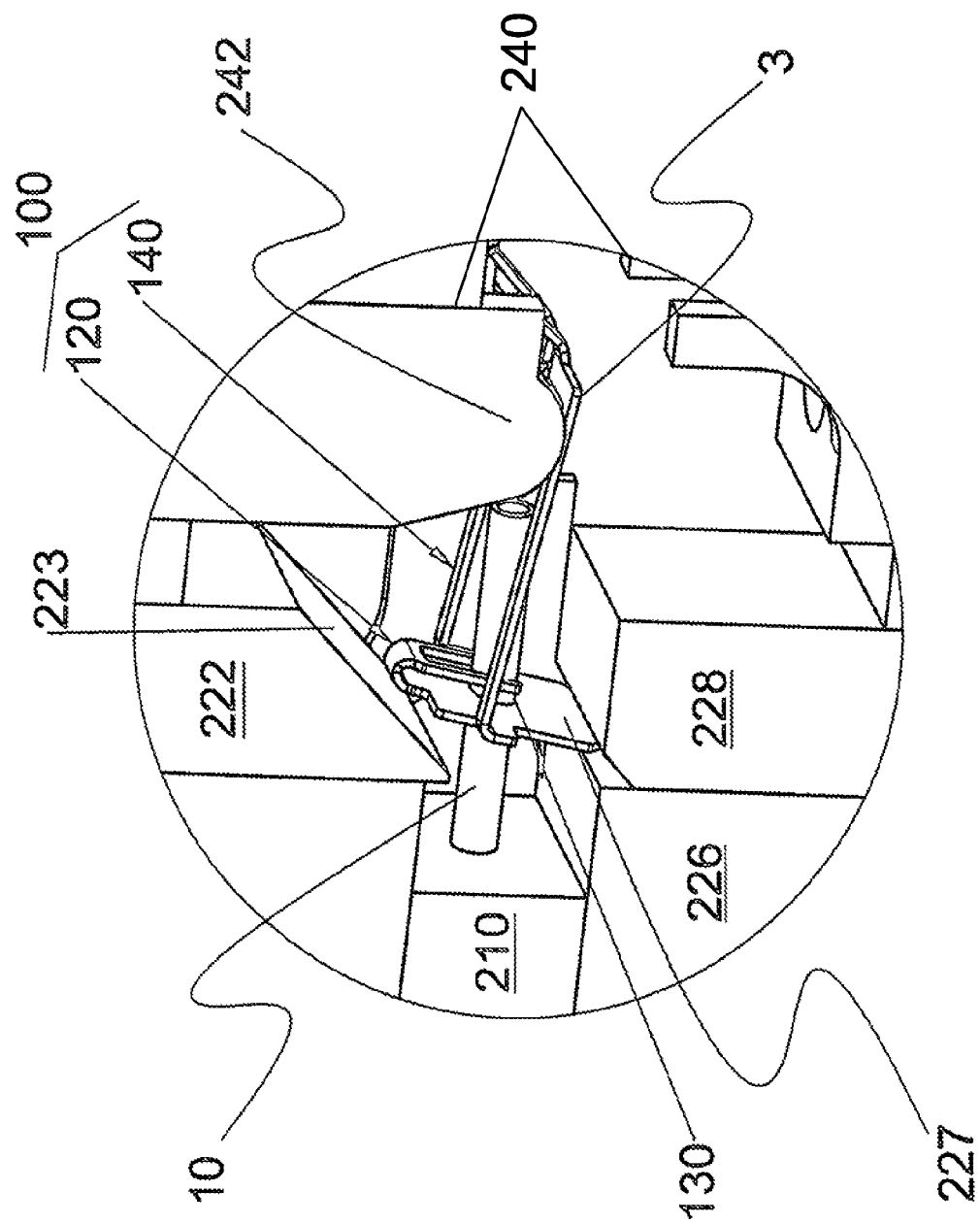
FIG. 2 is a perspective view of the binding member held and positioned by the retention tools such that it is in a desired position as provided in FIG. 1.

FIG. 2 shows the binding member 120 positioned by retention tools 220 such that it is in a desired position and is held appropriately to restrain unwanted movement. By restraining unwanted movement of binding member 120, end sensing member orientation tools 240 can further orient end sensing members 140. Orientation tools 240 comprise a top component 242 and a bottom component 244. Top component 242 is shown in FIG. 2 engaging the top surface of end sensing members 140.

Figure 3:
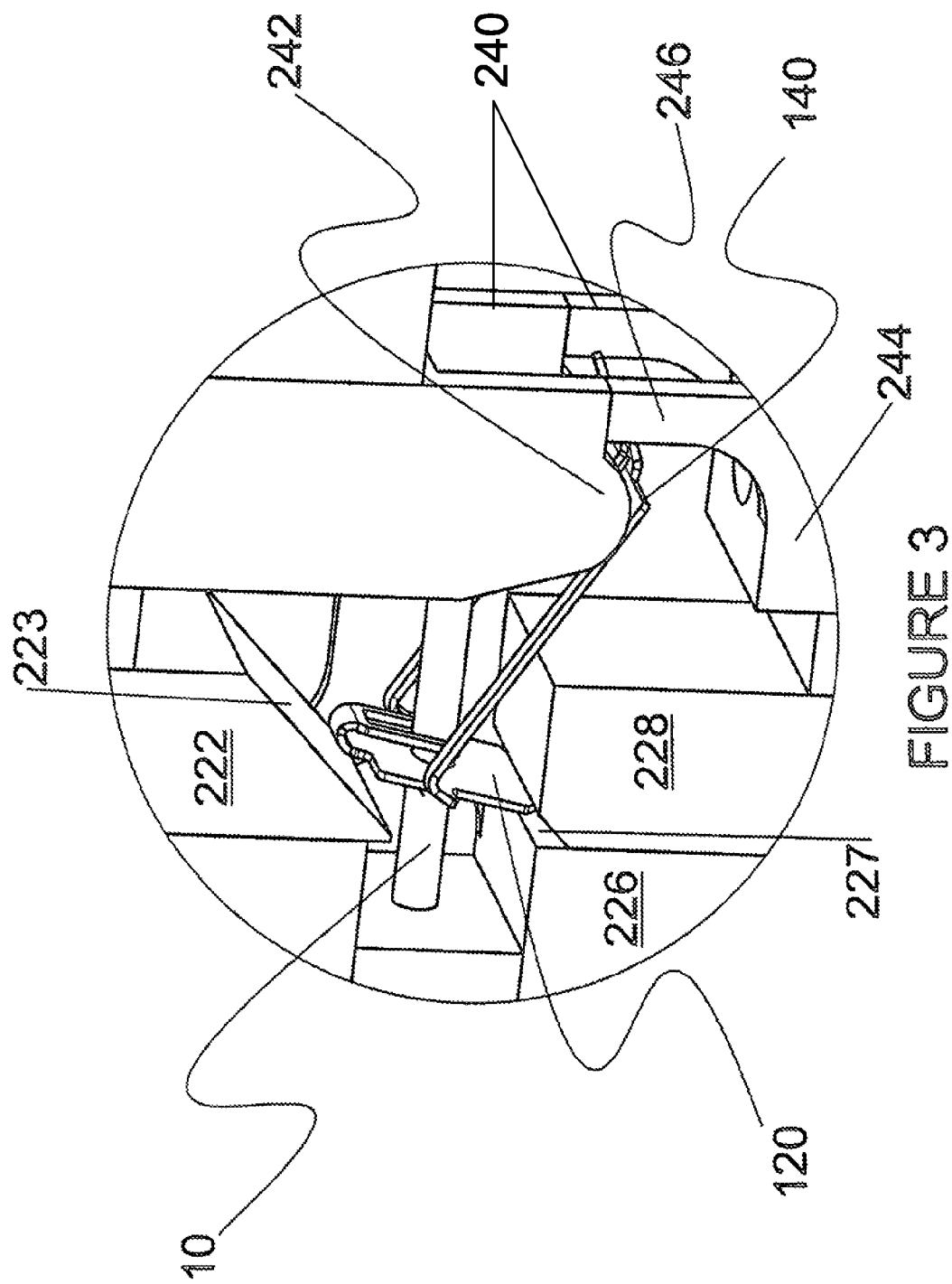
FIG. 3 is a perspective view which shows the top component of the orientation tools. The top component is shown pushing the end sensing members downward to cause plastic deformation of the metal while using the bottom component of the orientation tools as mechanical stop.

FIG. 3 shows top component 242 pushing against the top surface of end sensing members 140 such that it plastically deforms the metal of end sensing members 140. Bottom component 244 has prongs 246 which act as mechanical stops with respect to top component 242. The interaction of top component 242 and bottom component 244 of orientation tool 240 enable end sensing members 140 to be very precisely oriented and further shaped as needed.

Figure 4:
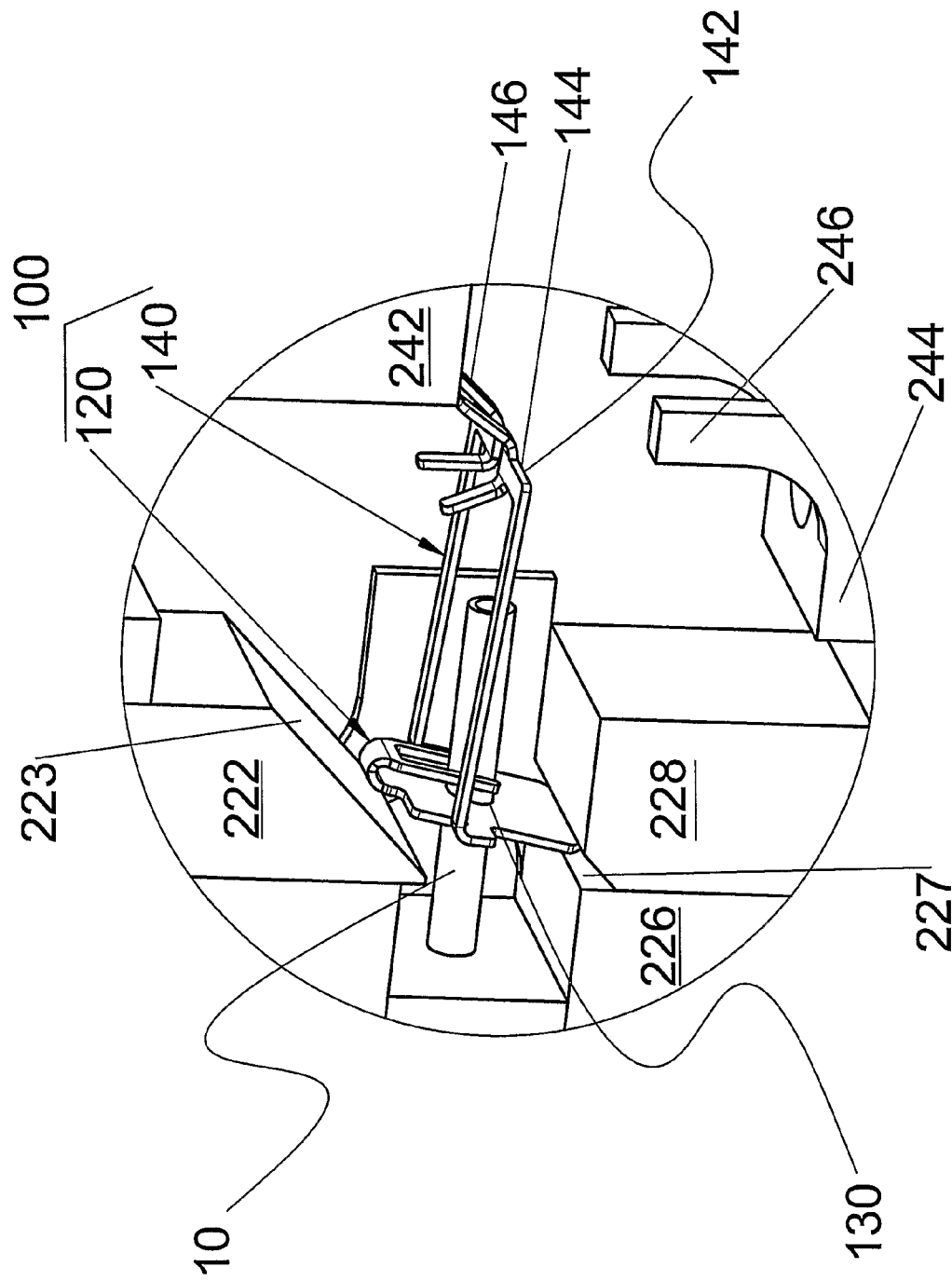
FIG. 4 is a perspective view of the plate with its end sensing member re-oriented such that the plate is ready to be moved into position on the medical needle for use.

FIG. 4 shows medical needle 10 with re-oriented end sensing members 140. Plate 100 is shown in FIG. 4 ready to be moved into position on medical needle 10 for use. Plate 100 is moved into position by advancing it on medical needle 10 until friction elements 146 engage medical needle 10 at a desired location.

FIGS. 5-7 depict another embodiment of re-orienting end sensing members as part of a method of manufacturing a medical needle shield apparatus. FIG. 5 shows the position of a sensor 250 which is used as part of a feedback loop. FIG. 6 shows top component 242 pushing against the top surface of end sensing members 140 such that it plastically deforms the metal of end sensing members 140 just like the step shown in FIG. 3. However, the step shown in FIG. 6 is achieved in combination with sensor 250 (not shown in FIG. 6). While FIG. 6 shows bottom component 244 and its prongs 246 acting as mechanical stops with respect to top component 242, the feedback loop can be used instead of, or in combination with, bottom component 244. The embodiment described with reference to FIGS. 5-7 enables the location of the end sensing members 140 to be discerned visually, electronically, or mechanically and for the information to be processed. The processed information can then be interpreted so that adjustments can be made as needed via top component 242 by displacing end sensing members 140 a certain amount based on the interpreted data. The loop cycles until the process discerns that the end sensing members are in the desired location. FIG. 7 depicts the completed loop with end sensing members 140 re-oriented.

FIGS. 8-12 depict an embodiment which utilizes the same principles described above with respect to the other embodiments. This embodiment also measures all of the appropriate dimensions that have relevance to the placement of end sensing members 140. The dimensional data is mathematically processed to predict where the end sensing members 140 need to be formed to end up in a desired location. This allows end sensing members 140 to be tailored to the needle and to be re-oriented similarly to the above embodiments.

The embodiment depicted in FIGS. 8-12 also utilizes an iterative process involving incremental revisions to the orientation of end sensing members 140 to "nudge" end sensing members 140 into a final orientation. The iterative process may be performed in combination with the feedback feature described above with respect to the embodiment detailed in reference to FIGS. 5-7.

Figure 8:
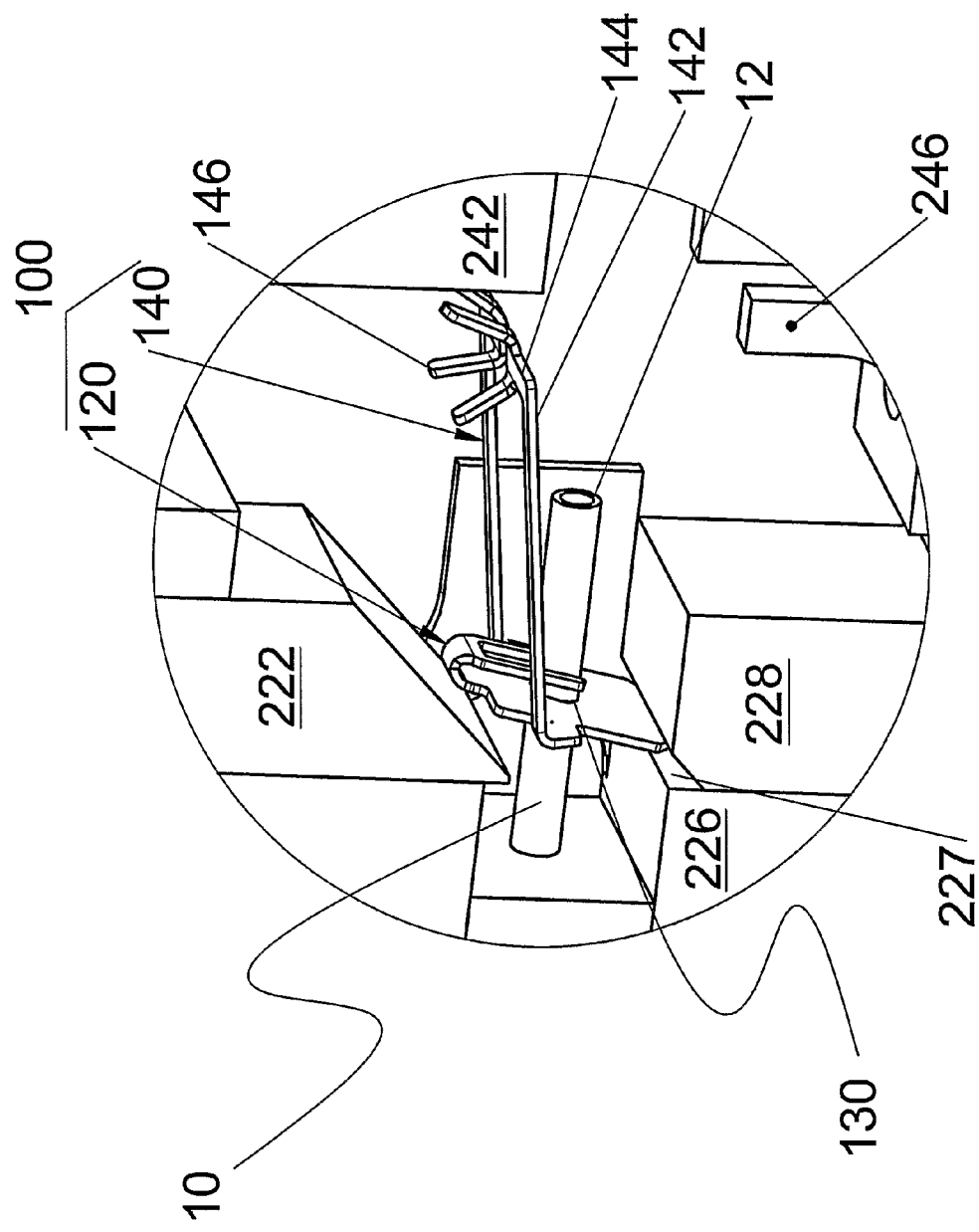
FIG. 8 a perspective view like the embodiment shown in FIG. 1.
Figure 9:
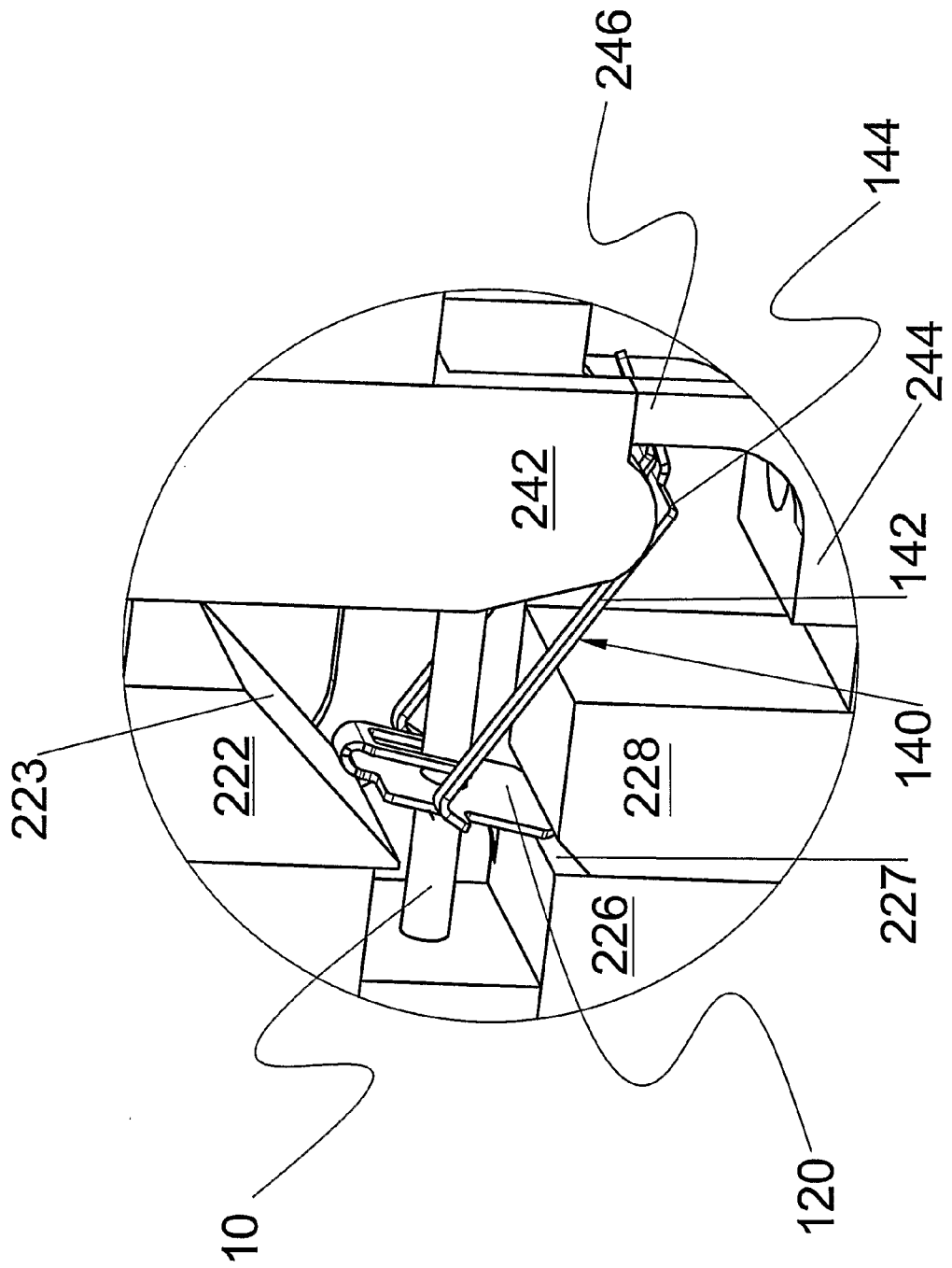
Figure 10:
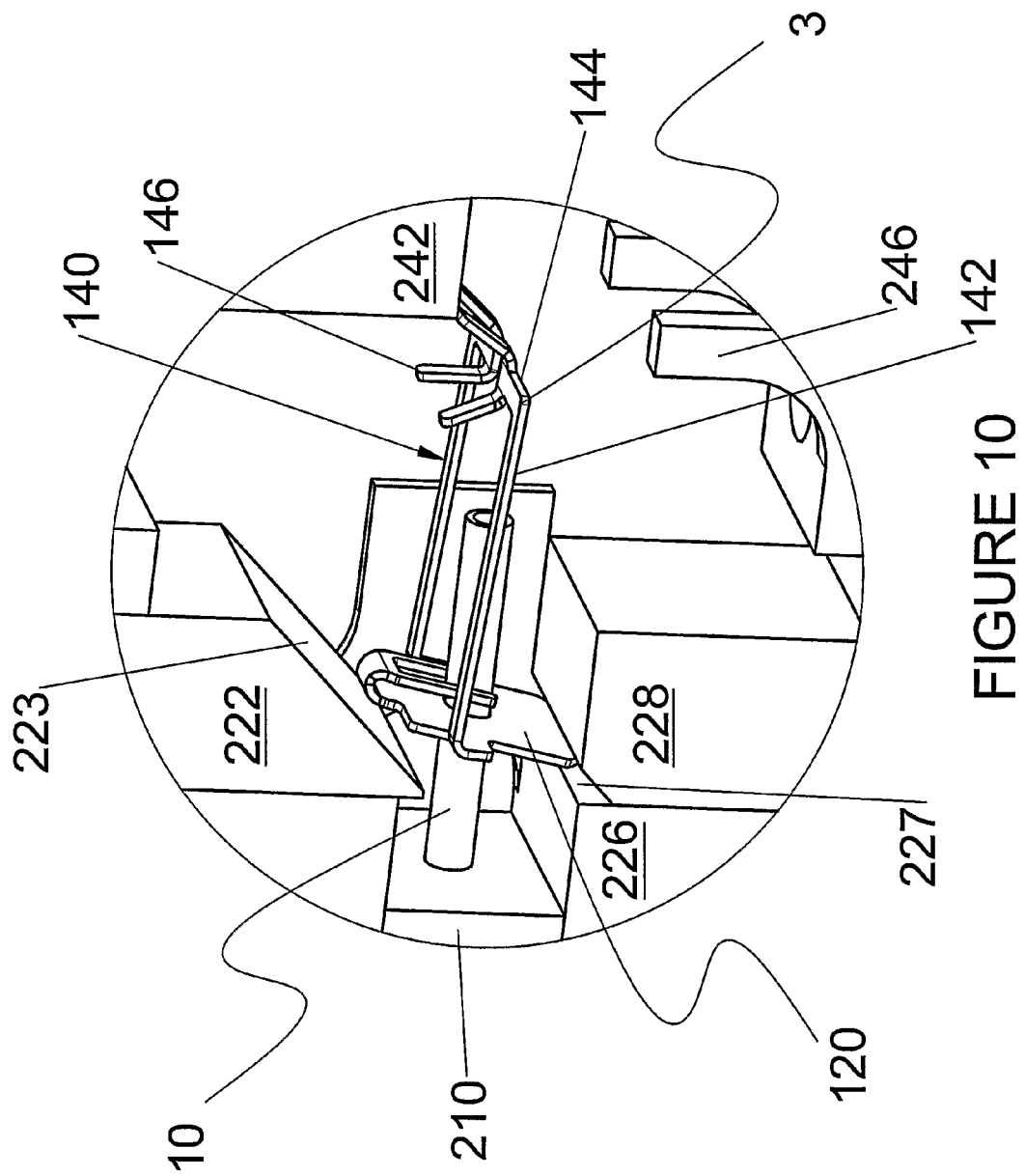
Figure 11:
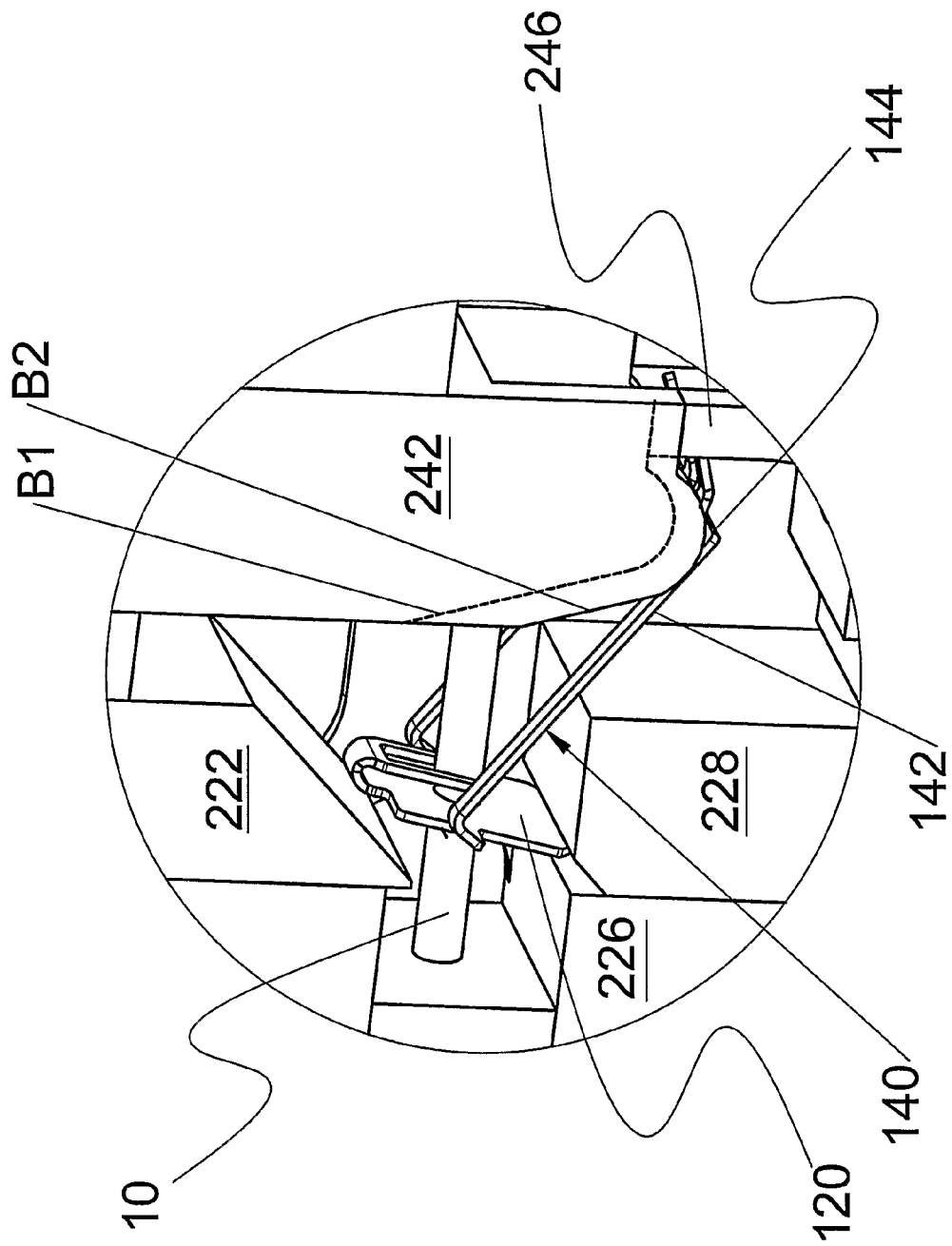
Figure 12:
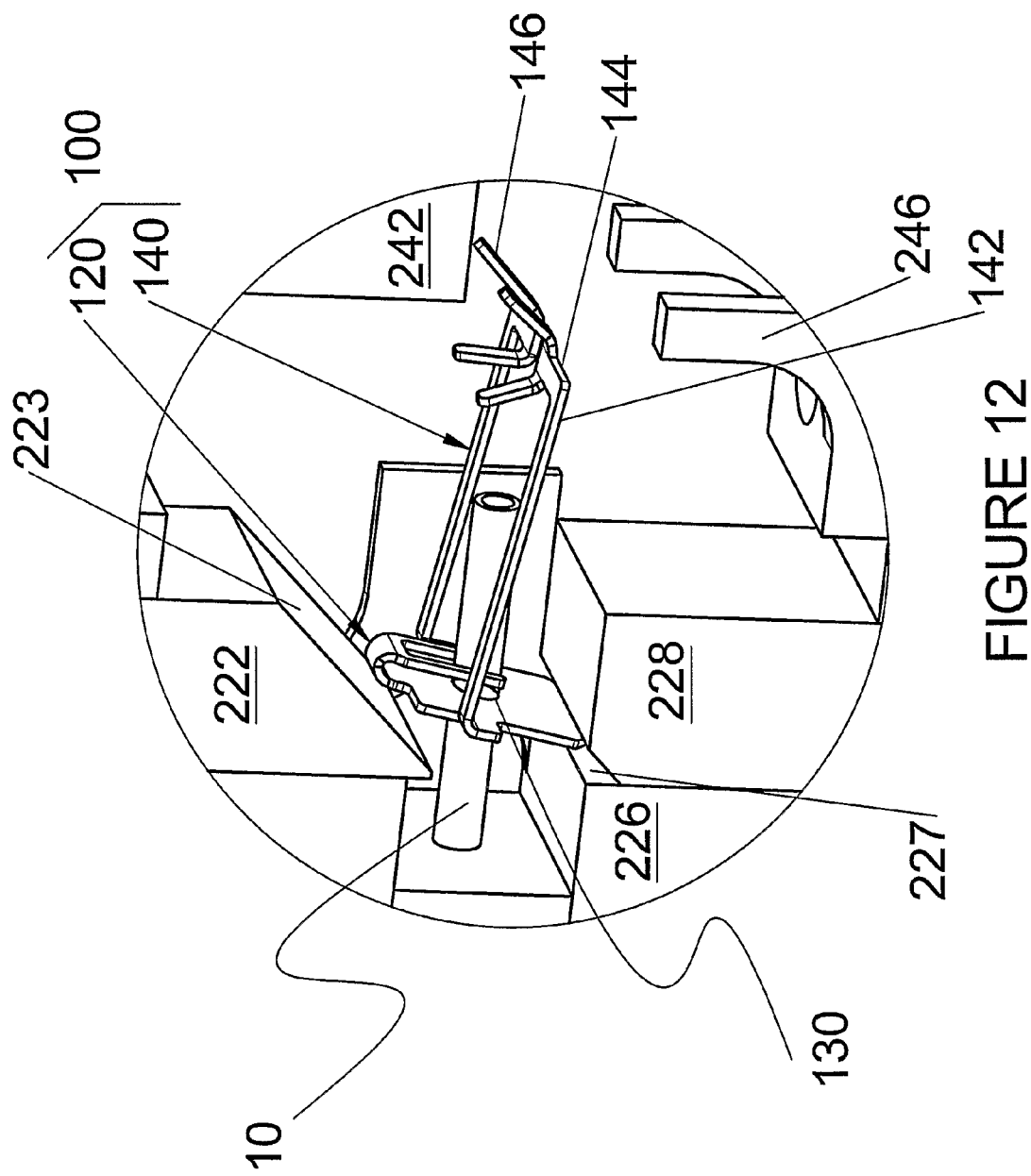

In the iterative process, plate 100 is positioned on medical needle 10 as shown in FIG. 8 which is identical to the image provided in FIG. 1. Note that while a sensor as shown in FIG. 5 is not depicted in FIG. 8, such a sensor can also be utilized with the embodiment depicted in FIGS. 8-12. FIG. 9 shows top component 242 pushing against the top surface of end sensing members 140 such that it plastically deforms the metal of end sensing members 140 just like the steps shown in FIG. 3 and FIG. 6. End sensing members 140 are then relaxed and evaluated for position requirements as shown in FIG. 10. As previously indicated, sensor 250 can be utilized as the evaluation tool to determine the position of end sensing members 140. FIG. 11 shows top component 242 proceeding to displace the end sensing members 140 again. FIG. 11 shows the first displacement of end sensing members 140 in phantom lines at B1 relative to the second displacement of end sensing members 140 as identified at B2. As shown in FIG. 11, the difference between the first displacement and second displacement is relatively small. As the displacement cycle is repeated, the metal plastically deforms in a corresponding increment. Again, the end sensing members 140 can be relaxed and evaluated for position as shown in FIG. 12.

FIGS. 13-15 depict three sequences in the iterative process of sequentially and incrementally adjusting the orientation of end sensing members 140. FIGS. 13-15 show three states of end sensing member 140 for each cycle and sequentially smaller adjustments. The three states include the initial or previous orientation A, the deflected position B, and the relaxed orientation C. FIG. 13 depicts the initial orientation A1, the deflected position B1 and the relaxed orientation C1. In FIG. 14, A2 is the same as C1 in FIG. 13. This process enables the end sensing members 140 to be stepped or nudged by small increments into position. Using small increments and evaluating the position allows the final position of end sensing members 140 to be precisely located.

The above description fully discloses the invention including preferred embodiments thereof. Without further elaboration, it is believed that one skilled in the art can use the preceding description to utilize the invention to its fullest extent. Therefore the examples and embodiments disclosed herein are to be construed as merely illustrative and not a limitation of the scope of the present invention in any way.

It will be apparent to those having skill in the art that changes may be made to the details of the above-described embodiments without departing from the essential characteristics and underlying principles of the invention. Embodiments of the invention in which an exclusive property or privilege is claimed are defined as follows.

The invention claimed is:

1. A method for manufacturing a medical needle shield apparatus comprising:
   placing a binding member of a friction based plate on a medical needle while an end sensing member of the friction based plate remains off of the medical needle,
   retaining the binding member,
   re-orienting the end sensing member while the binding member is retained, and
   positioning the end sensing member on the medical needle after the end sensing member has been re-oriented, wherein the binding member is retained by a shaping device and the shaping device is used to re-orient the end sensing member.

2. The method of claim 1, wherein the binding member has at least one aperture defined by binding surfaces and the medical needle extends through the aperture.

3. The method of claim 1, wherein the end sensing member and another end sensing member extend from the binding member to provide a dual end sensing members.

4. The method of claim 1, wherein the end sensing member comprises friction elements which engage the medical needle.

5. The method of claim 1, wherein the binding member is retained by at least one retention tool.

6. The method of claim 1, wherein the binding member is retained and oriented by retention tools.

7. The method of claim 1, wherein the end sensing member is re-oriented by at least one orientation tool.

* * * * *